(12) United States Patent
Roy

(10) Patent No.: US 11,671,260 B2
(45) Date of Patent: Jun. 6, 2023

(54) EXPIRING SOFTWARE KEY FOR UNLOCKING A MODE ON A DEVICE

(71) Applicant: Medtronic, Inc., Minneapolis, MN (US)

(72) Inventor: Arindam Ghosh Roy, Bangalore (IN)

(73) Assignee: Mozarc Medical US LLC, Minneapolis, MN (US)

( * ) Notice: Subject to any disclaimer, the term of this patent is extended or adjusted under 35 U.S.C. 154(b) by 0 days.

(21) Appl. No.: 17/318,341

(22) Filed: May 12, 2021

(65) Prior Publication Data
US 2022/0368529 A1 Nov. 17, 2022

(51) Int. Cl.
*H04L 9/32* (2006.01)
*H04L 9/08* (2006.01)
*A61M 1/16* (2006.01)
*A61M 1/28* (2006.01)

(52) U.S. Cl.
CPC ......... *H04L 9/3234* (2013.01); *A61M 1/1601* (2014.02); *A61M 1/282* (2014.02); *H04L 9/0891* (2013.01)

(58) Field of Classification Search
CPC ................ H04L 9/3234; H04L 9/0891; A61M 1/1601; A61M 1/282
See application file for complete search history.

(56) References Cited

U.S. PATENT DOCUMENTS

| | | | | |
|---|---|---|---|---|
| 8,639,770 B1 * | 1/2014 | Raley | .................... | G06F 16/172 709/216 |
| 9,300,639 B1 * | 3/2016 | Roth | ................... | H04L 63/0807 |
| 11,243,982 B2 * | 2/2022 | Hoeppner | ............... | G06F 16/22 |
| 2009/0198899 A1 * | 8/2009 | Revanuru | ........... | G06F 12/0848 711/E12.017 |
| 2011/0196940 A1 * | 8/2011 | Martinez | ................... | H04L 9/40 709/217 |
| 2016/0241403 A1 * | 8/2016 | Lindemann | ........... | H04L 9/3247 |
| 2017/0173262 A1 * | 6/2017 | Veltz | ..................... | G16H 20/17 |
| 2019/0220617 A1 * | 7/2019 | Harriman | ............ | G06F 21/6218 |
| 2020/0356687 A1 * | 11/2020 | Salzman | ............... | H04L 63/108 |
| 2021/0319139 A1 * | 10/2021 | Ruan | ........................ | G06F 21/73 |
| 2022/0158846 A1 * | 5/2022 | Ray | ........................ | H04L 9/0825 |
| 2022/0229748 A1 * | 7/2022 | Ostrikov | ............. | G06F 11/1417 |

FOREIGN PATENT DOCUMENTS

| | | |
|---|---|---|
| EP | 0640945 | 3/1995 |
| WO | 2010057423 | 5/2010 |

OTHER PUBLICATIONS

European Search Report for App. No. 20194964.1, dated Dec. 8, 2020.
Li Xiong, et al., "An Enhancement of a Smart Card Authentication Scheme for Multi-server Architecture", Wireless Personal Communications, Springer, Dordrecht, NL, vol. 80, No. 1, Aug. 19, 2014, pp. 175-192.

* cited by examiner

*Primary Examiner* — Mohammad A Siddiqi
(74) *Attorney, Agent, or Firm* — Hahn & Associates

(57) ABSTRACT

A security token is provided having a communication interface with a communication transceiver; a circuit having encoded thereon an immutable hardware key; and a tangible, nonvolatile memory, the nonvolatile memory having stored thereon a mutable software key, the mutable software key including a cryptographic key and an expiry for the cryptographic key.

6 Claims, 8 Drawing Sheets

EXPIRING SOFTWARE KEY FOR UNLOCKING A MODE ON A DEVICE

FIELD

Systems and methods are disclosed for providing an expiring software key for unlocking a mode on a device or apparatus requiring security. The systems and methods are related to any apparatus or device requiring security, and more particularly, but not exclusively, to a biomedical device having an expiring software key for unlocking a mode on the biomedical device.

BACKGROUND

Instruments and hardware require security for general computing, cryptography, data centers, cloud processing, autonomous vehicles, wearable computers, internet of things (IoT) devices, and mobile computing, and by way of non-limiting example, biomedical devices. Hardware tokens are sometimes used to provide security, but can present a security risk if they are lost or stolen. A lost or stolen hardware token can be found, or deliberately taken, by an adversary or other unauthorized user. The adversary or other unauthorized user can then use the hardware token to enter an access-controlled mode of a device and perform malicious or other unauthorized activities. The problem can be exacerbated in a financial or healthcare setting having sensitive information. In finance, personal information and sensitive banking information can be compromised. In healthcare, devices used to provide therapeutic treatment or otherwise improve the functioning of the human body rely on access-controlled functions and modes to support human life and health. However, biomedical devices and other therapeutic can be at risk of a security breach using the known components and methods.

One example of a medical device is a dialysis machine or hemodialysis machine. A hemodialysis machine replaces the functions of the human kidney by extracting blood from the patient, cleaning the blood, such as by filtering or otherwise extracting impurities, optionally performing other chemical processes on the blood, and replacing the filtered blood to the patient. A peritoneal dialysis machine delivers a peritoneal dialysis fluid into a patient and remove used fluid after a dwell period. Such devices commonly have different modes of operation, and the different modes may need to be protected against unauthorized access. The devices may contain treatment prescription specific for a particular patient. The devices may also have components that are only suitable or matched to a specific patient. The devices may be used in a clinical or hospital setting where unauthorized persons or devices may come into contact physical or wireless contact with the machines. The machines may have a plurality of modes, and may include access control mechanisms to control access to the plurality of modes. For example, calibration of the components of a dialysis machine can be performed in a so-called "service mode" of the machine. However, if an unauthorized user performs calibration on the machine incorrectly, this could harm the device, or even worse, harm the patient.

To block unauthorized users from unauthorized access to the machine, a hardware token is one common mechanism to control access to the modes of a device. A hardware token may include a physical device that can be used by an authorized user to authenticate himself or herself to the machine. For example, in the case of a USB hardware access token, the user may insert the token into a USB drive. In the case of an RFID access token, proximity to the device may be sufficient. The device can then allow access to the access-controlled modes only when the valid hardware token is correctly presented. However, hardware tokens present a security risk if they are lost or stolen. A typical requirement to minimize a security risk posed by a hardware token would be to manually update the information on revoked hardware tokens for each and every device to perform a successful revocation. This can be unduly cumbersome, particularly where a clinic or enterprise operates more than one device. Moreover, propagating such revocations can be a challenge, particularly if the devices are not connected to a central network, as is common in some use cases for biomedical devices. Revoking access may be problematic if the devices are not controlled from a central control center and/or if the devices do not have internet access. Even if the devices have internet access, intermittent or poor internet access can complicate a central control model.

Hence, there is a need to block unauthorized users from unauthorized access to a machine or device. There is a related need to revoke access to a hardware token and/or control access to one or more modes of a machine or device. There is still further related need to revoke access to a hardware token and/or control access to a non-networked machine or device. There is a need for a hardware token that is not limited to a physical device but that can be used by an authorized user to authenticate himself or herself to the machine. There is a need for a method to reduce the security risk for devices with controlled access modes independent of central control and/or internet access. There is still further a need to provide revocation mechanisms, whereby the access of a particular hardware token can be revoked in a controlled and specified manner. There is a need to provide revocation mechanisms, whereby the access of a particular hardware token can be revoked after a certain period of time. There is a need for a mechanism to control access to a device, including a non-networked biomedical device. There is still further a need for providing a full hardware token revocation mechanism, and without the need for a persistent network connection.

SUMMARY OF THE INVENTION

The first aspect relates to a security token. In any embodiment, the security token may include: a communication interface, including a communication transceiver; a circuit having encoded thereon an immutable hardware key; and a tangible, nonvolatile memory, the nonvolatile memory having stored thereon a mutable software key, the mutable software key including a cryptographic key and an expiry for the cryptographic key.

In any embodiment, the mutable software key may be a data structure selected from the group consisting of JSON, BSON, XML, MessagePack, and YAML.

In any embodiment, the data structure may be signed or encrypted.

In any embodiment, the expiry may include an initial valid time and a validity time span.

In any embodiment, the validity time span may be approximately 24 hours.

In any embodiment, the validity time span may be approximately 7 days.

In any embodiment, the validity time span may be between approximately 24 hours and approximately 7 days.

In any embodiment, the validity time span may be approximately 14 days.

In any embodiment, the validity time span may be approximately 28 days.

In any embodiment, the validity time span may be between approximately 24 hours and 28 days.

In any embodiment, the communication interface may include a universal serial bus (USB) port.

In any embodiment, the communication interface may be selected from the group consisting of universal serial bus (USB), a radio frequency identification (RFID) transceiver, a Bluetooth transceiver, a WiMax transceiver, an infrared transceiver, a serial bus, or a parallel port bus.

In any embodiment, the communication interface may include a network interface.

The features disclosed as being part of the first aspect can be in the first aspect either alone or in combination, or follow any arrangement or permutation of any one or more of the described elements. Similarly, any features disclosed as being part of the first aspect can be in a second, third, or fourth, aspect described below, either alone or in combination, or follow any arrangement or permutation of any one or more of the described elements.

The second aspect relates to a system. In any embodiment, the system may include an apparatus programmed to provide a plurality of modes, and the security token of any previous embodiment of the first aspect, wherein the apparatus includes: a processor and a memory; a communication interface; and instructions encoded within the processor to: provide the plurality of modes, including a restricted mode; detect the security token via the communication interface; cryptographically verify the immutable hardware key of the security token; and activate the restricted mode after verifying that the mutable software key is valid and unexpired.

In any embodiment, the system may include a therapeutic subsystem to administer a therapeutic treatment to a patient, wherein the restricted mode includes a therapy administration mode.

In any embodiment, the system may include a dialysis machine.

In any embodiment, cryptographically verifying the immutable hardware key may include verifying that the immutable hardware key has not expired.

In any embodiment, verifying that the mutable software key is valid and unexpired may include extracting the expiry from the mutable software key.

In any embodiment, verifying that the mutable software key is valid and unexpired may include cryptographically validating the mutable software key.

In any embodiment, cryptographically validating the mutable software key may include validating the mutable software key via the immutable hardware key.

In any embodiment, cryptographically validating the mutable software key may include validating the mutable software key via a shared key stored on the security token.

In any embodiment, cryptographically validating the mutable software key may include querying a certificate authority.

The features disclosed as being part of the second aspect can be in the second aspect, either alone or in combination, or follow any arrangement or permutation of any one or more of the described elements. Similarly, any features disclosed as being part of the second aspect can be in the first, third, or fourth aspect described below, either alone or in combination, or follow any arrangement or permutation of any one or more of the described elements.

The third aspect relates to a controller for a medical apparatus. In any embodiment, the controller can include a microcontroller; a memory; and software encoded within the memory to instruct the microcontroller to: interface with an input/output device; detect, via the input/output device, a physical or logical connection of a hardware token; receive, via the input/output device, an immutable hardware key of the hardware token; retrieve, via the input/output device, a mutable software key stored in a memory of the hardware token; validate the immutable hardware key and the mutable software key, including verifying that the mutable software key is valid and not expired; and responsive to the validating, enable a mode selected from a plurality of operating modes of the controller.

In any embodiment, validating the immutable hardware key may include verifying that the immutable hardware key has not timed out.

In any embodiment, validating the mutable software key may include extracting an expiry from the mutable software key.

In any embodiment, the mutable software key may include a JSON data structure.

In any embodiment, the JSON data structure may be signed or encrypted.

In any embodiment, validating the mutable software key may include cryptographically validating the mutable software key.

In any embodiment, cryptographically validating the mutable software key may include validating the mutable software key via the immutable hardware key of the hardware token.

In any embodiment, cryptographically validating the mutable software key may include validating the mutable software key via a shared key stored on the medical apparatus.

In any embodiment, cryptographically validating the mutable software key may include validating the mutable software key via an immutable hardware key stored on the medical apparatus.

In any embodiment, cryptographically validating the mutable software key may include querying a certificate authority.

In any embodiment, validating the mutable software key may include computing an expiration from an initial valid time stored in a data structure of the mutable software key and a time span stored in the data structure.

In any embodiment, the time span may be approximately 24 hours.

In any embodiment, the time span may be approximately 7 days.

In any embodiment, the time span may be between approximately 24 hours and approximately 7 days.

In any embodiment, the time span may be approximately 14 days.

In any embodiment, the time span may be approximately 28 days.

In any embodiment, the time span may be between approximately 24 hours and 28 days.

In any embodiment, the input/output device may include a universal serial bus (USB) port.

In any embodiment, the input/output device may be selected from the group consisting of universal serial bus (USB), a radio frequency identification (RFID) transceiver, a Bluetooth transceiver, a WiMax transceiver, an infrared transceiver, a serial bus, or a parallel port bus.

In any embodiment, the input/output device may include a network interface.

In any embodiment, the controller may be included in a security token.

In any embodiment, the controller may be included in a security token, and the medical apparatus may be a dialysis machine.

The features disclosed as being part of the third aspect can be in the third aspect, either alone or in combination, or follow any arrangement or permutation of any one or more of the described elements. Similarly, any features disclosed as being part of the third aspect can be in the first, second, or fourth aspect either alone or in combination, or follow any arrangement or permutation of any one or more of the described elements.

The fourth aspect relates to a software token server apparatus. In any embodiment, the token server apparatus can include a hardware platform including a processor and a memory; a network interface; and instructions encoded within the memory to instruct the processor to: receive, via the network interface, from a client device, a request for a time-limited software token to be stored on a hardware token; generate a software key, including generating an expiry for the software key; and sending, via the network interface, the software key to the client device.

In any embodiment, the instructions may receive, via the network interface, an immutable hardware key of the hardware token, and associate the immutable hardware key with the software key.

In any embodiment, associating the immutable hardware key with the software key may include signing the software key with the immutable hardware key.

In any embodiment, associating the hardware token with the software key may include encrypting the software key with the hardware token.

In any embodiment, the instructions may associate the software key with a selected user device.

In any embodiment, associating the software key with the selected user device may include retrieving from a database an immutable hardware key of the selected user device, and signing and/or encrypting the software key with the immutable hardware key.

In any embodiment, associating the software key with the selected user device may include retrieving from a database a shared key previously provisioned to the selected user device, and signing and/or encrypting the software key with the shared key.

In any embodiment, the selected user device may be a biomedical device having a plurality of operating modes, including a restricted mode that can be unlocked via a combination of the hardware token and the software key.

In any embodiment, generating the expiry for the software key may include time-stamping the software key with a time that the software key was generated, and adding a span during which the software key is valid.

In any embodiment, the span may be approximately 24 hours.

In any embodiment, the span may be approximately 7 days.

In any embodiment, the span may be between approximately 24 hours and approximately 7 days.

In any embodiment, the span may be approximately 14 days.

In any embodiment, the span may be approximately 28 days.

In any embodiment, the span may be between approximately 24 hours and 28 days.

The features disclosed as being part of the fourth aspect can be in the fourth aspect either alone or in combination, or follow any arrangement or permutation of any one or more of the described elements. Similarly, any features disclosed as being part of the fourth aspect can be in the first, second, or third aspect either alone or in combination, or follow any arrangement or permutation of any one or more of the described elements.

DETAILED DESCRIPTION

Figure 1:
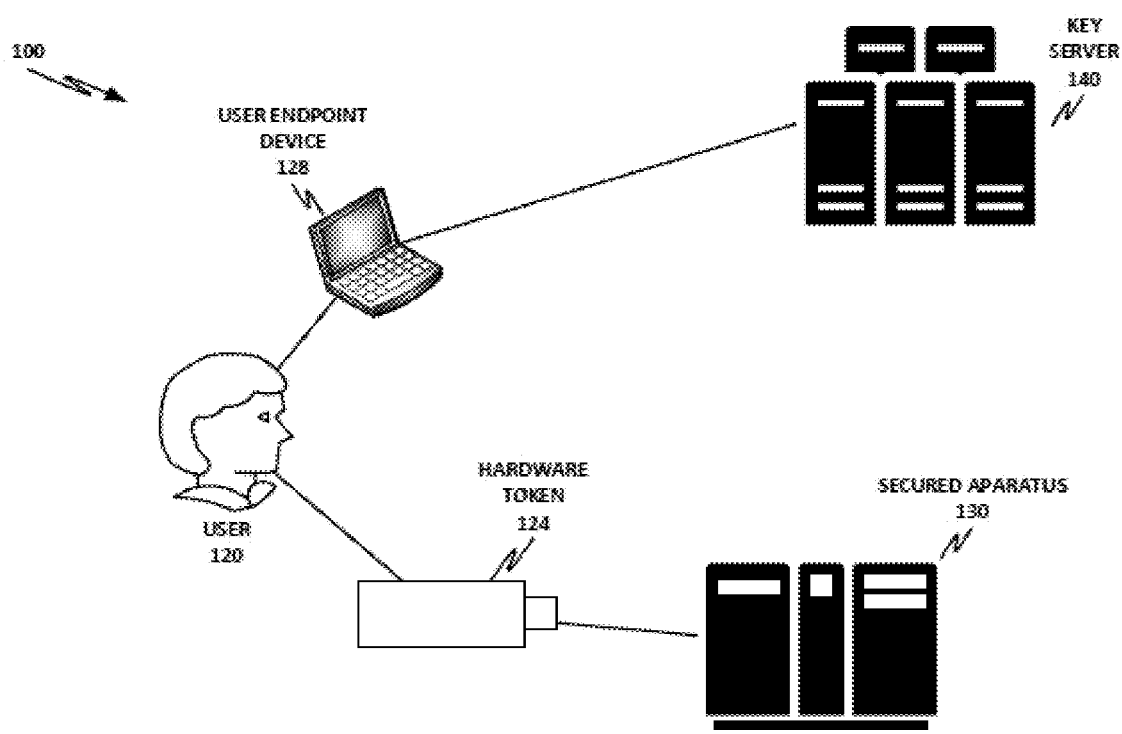
FIG. 1 is a block diagram of a device ecosystem.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "administration mode" generally refers to any mode of operation in which a user, device, server, computer, or controller has access to administrative, or relatively unrestricted, operations.

The term "approximately" refers to the same value, or nearly the same value.

The term "associate" refers to logically connecting or linking one datum to another.

The term "biomedical device" refers to a device that provides therapy, monitoring, or telemetry for a biological entity, and most particularly, for a human. Biomedical devices may passively monitor a human patient, or they may actively administer a therapeutic service.

The term "Bluetooth" refers to a wireless communication standard generally used over relatively short distances, usually employing waves in the 2.402 to 2.480 gigahertz (GHz) band.

The term "BSON (Binary JSON)" refers to a binary form for representing data for interchange.

The term "certificate authority" refers to a trusted entity that operates a server that issues cryptographic certificates. When a certificate is to be verified, the certificate authority can be queried, or a cached cryptographic hash from the certificate authority can be used to verify the certificate.

The term "circuit" refers to any electronic analog, digital, or mixed-signal electronic network or software implemented network. In the case of digital or mixed-signal networks, the circuit may also include instructions or other inputs that are used to program the circuit. In the case of a software implemented network, the circuit can be implemented in programmed instructions in a platform configured to carry the instructions.

The term "client device" refers, in a client-server architecture, to a device that receives services from the server. Generally, the client device makes an outgoing connection to the server, and receives data or other services from the server. In common usage, the client device is most often the device operated by an end user.

The term "communication interface" refers to any hardware, software, and combinations thereof that provides a mechanism for a device to communicatively couple to another device, and to communicate. The devices could be active or passive devices. For example, Ethernet is generally used to couple active devices to one another. A protocol such as universal serial bus (USB) may be used to communicatively couple an active device to a passive device.

The term "communication transceiver" refers to any hardware, software, and combinations thereof that thereof that can provide transmitter and receiver functions.

The term "cryptographically validate" refers to the use of a cryptographic algorithm to determine that an object is what the object claims to be, and has not been tampered with.

The term "cryptographically verify" refers to the use of a cryptographic algorithm to determine the authenticity or validity of data. Nonlimiting examples of cryptographic algorithms include DES, RSA, AES, Blowfish, Twofish, IDEA, MD5, and HMAC.

The term "cryptographic key" refers to a hash, certificate, secret, or other datum that can be used to encrypt, decrypt, or cryptographically verify another datum, device, or object.

The term "database" refers to a structured data storage system, in which data are stored in a way that they can be queried and retrieved, according to designated fields.

The term "data structure" refers to any organized sequence of data in any form.

The term "encrypted" refers to data encoded into a non-human-readable format, by way of an encryption key, keys, key pair, password, passphrase, hash, or other datum or data used to reconfigure data so that they are not usable without a key, password, hash, or other cryptographic token.

The term "expired" refers to an object that is past a designated expiry time.

The term "expiry" refers to a time at which an object becomes invalid, or is no longer usable.

The term "hardware key" refers to a cryptographic key that is stored in a hardware device, and is hardcoded into the device such that the device cannot be removed via ordinary, nondestructive means.

The term "hardware platform" refers to an electronic device that may include a mix of analog, digital, and mixed-signal circuits to carry out an algorithm.

The term "immutable" refers to a property or datum associated with an electronic device that cannot be changed via ordinary operation of the device, or absent destructive means.

The term "infrared" refers to a wireless communication standard that uses pulses of infrared light, and generally requires line of sight between devices.

The term "initial valid time" refers to a start time for the validity of an object.

The term "input/output (I/O) device" refers to an apparatus, including circuitry and logic, that enables a device to receive inputs and to send outputs to another device or to a human user.

The term "instructions" refers to machine-readable data that cause a processor to execute an algorithm. In the case of a microprocessor or microcontroller, the instructions may be a series of operation codes that, in a particular sequence, cause the processor to execute a desired algorithm. In the case of an FPGA or ASIC, the instructions may be written in a hardware description language that is used to configure the circuit to carry out the algorithm.

The term "JSON (JavaScript Object Notation)" refers to an open-standard file format for data interchange.

The term "logical connection" refers to a connection between two devices, in which data may be transferred, either via wires or wirelessly. The "logical connection" can also include a status in which two devices are communicatively coupled to one another such that each provides the necessary logic to exchange data with the other, either via a wired connection or wirelessly.

The term "MessagePack" refers to a binary data interchange format.

The term "memory" refers to an electronic medium capable of storing encoded data.

The term "microcontroller" refers to a programmable circuit that executes an instruction set that is generally more limited than a more comprehensive instruction set that is executable by a microprocessor. In general terms, a microcontroller has fewer transistors than a microprocessor, provides fewer instructions, draws less power, and usually operates at lower clock speeds.

The term "mode" refers to an operational construct, in which hardware or software may operate with different capabilities, permissions, or functions, depending on the configuration of the mode. Each mode may have designated conditions or prerequisites, and may be designed to enable certain functions to be carried out in the mode.

The term "mutable" refers to a property or datum of an electronic device that can be altered using ordinary, nondestructive means.

The term "network interface" refers to a hardware and software stack that provides the physical interconnects, protocols, and drivers to enable a computing device to communicate with other devices via a private or public network.

The term "nonvolatile memory" refers to a data storage medium that retains stored data when power is removed.

The term "parallel port" refers to a wired communication protocol in which a data byte or word is sent in parallel over a plurality of transmission lines. A parallel port may conform to the IEEE 1284 standard, or use some other parallel communication protocol.

The term "plurality" refers to more than one.

The term "physical connection" refers to a connection between two devices, wherein communication is facilitated by physical contact, such as via physical wires.

The term "processor" refers to a programmable or configurable logic circuit, which can be configured to execute a desired algorithm. A processor may provide a generalized instruction set, such as in the case of a microprocessor or microcontroller, or may be configured in hardware as in the case of an application-specific integrated circuit (FPGA). In some cases, processors may be emulated and/or virtualized. For example, virtualization technology may provide a virtual processor running under a hypervisor, or other kind of virtualization layer, in which case the "processor" may include the emulation layer, as well as the physical processor that ultimately executes the instructions.

The term "restricted mode" refers to any mode of operation that cannot be entered except by a person or device that has been authorized to enter the mode.

The term "RFID (radiofrequency identification)" refers to a technology that uses electromagnetic fields to identify and track a device. An RFID device includes a radio transponder, which generally is triggered by proximity to an RFID reader device. The RFID reader device sends a pulse, which the RFID device detects, and responds to. RFID devices can be either active or passive.

The term "security token" refers to a hardware or software token that may be used to cryptographically authenticate or otherwise authorize a person or device to perform an action requiring said authentication or authorization.

The term "serial bus" refers to a wired communication protocol in which data are sent serially, or one bit at a time, over the bus. Examples of serial buses include RS-232, RS-485, serial peripheral interface (SPI), inter-integrated circuit (I2C), UNI/O, 1-Wire, and PCI Express (PCIe).

The term "server" refers, in a client-server architecture, to a device, computer, or cloud infrastructure that accepts incoming connections, and provides services to one or more client devices.

The term "shared key" refers to a cryptographic key that is distributed to a plurality of devices or actors, so that the devices or actors can cryptographically verify the same data.

The term "signed" generally refers to a datum accompanied by a cryptographic hash or other key that can be used to verify authenticity and/or integrity. Any other form of suitable signature known to one of skill is contemplated.

The term "software key" refers to a cryptographic key stored in a rewritable storage medium, which can be altered using ordinary, non-destructive means.

The term "tangible" refers to a physical apparatus that can be held and manipulated by a human actor.

The term "therapeutic subsystem" refers to a portion of a medical apparatus that administers therapy or treatment to a patient.

The term "therapeutic treatment" refers to a medical procedure, which may be carried out by a machine, wherein a pharmaceutical substance is administered to a patient, or a medical procedure is performed on or for the patient.

The term "therapy administration mode" refers to a mode of operation in which a user, device, or controller may administer settings for therapy.

The term "timed out" refers to reaching a designated expiry.

The term "transceiver" refers to any hardware, software, or combinations thereof that can provide transmitter and receiver functions.

The term "unexpired" refers to not past a designated expiry time.

The term "USB (universal serial bus)" refers to an industry standard that specifies cables, connectors, and protocols for communicating serially.

The term "valid" refers, in the case of a security token, to the token passing a cryptographic verification, and that the token is not expired.

The term "validity time span" refers to a quantum of time, such as in seconds, milliseconds, or other time measure, during which an object is valid. The validity time span may commence at an initial valid time, and may last for a quantum of time, or may be designated as a time or date certain, at which the object will expire.

The term "WiMAX" is an acronym for "worldwide interoperability for microwave access," referring to a family of wireless communication standards that provide both a physical layer (PHY), and media access control (MAC). WiMAX is governed by the IEEE 802.16 set of standards.

The term "XML (Extensible Markup Language)" refers to a data structure that follows a set of rules for encoding documents in a human-readable format that is also machine-readable.

The term "YAML" is a recursive acronym for "YAML Ain't Markup Language," referring to a particular human-readable data serialization language.

Device Ecosystem

FIG. 1 is a block diagram of a device ecosystem 100. Device ecosystem 100 includes a secured apparatus 130. Secured apparatus 130 could be, for example, a server, computer, or device of any type. In one non-limiting embodiment, the secured apparatus 130 is a biomedical device such as a therapeutic device. In one embodiment, the secured apparatus 130 can be a hemodialysis machine, peritoneal dialysis machine, and/or any related components used for providing therapy, such as a cycler or a dialysis fluid preparation component. Although one secured apparatus 130 is illustrated in this embodiment, a plurality of secured apparatus could be provided. For example, a plurality of secured apparatus 130, ecosystem 100 could be, for example, a clinic or hospital that provides a plurality of dialysis machines. If the clinic is located, for example, in an inconvenient or difficult setting or location for each machine to have an always-on internet connection, manually revoke rights from a hardware token for each machine in the group may be cumbersome or impossible. These machines could be a subset, such as any more than two machines of the same model, which may be fewer than all of the examples of that model. For example, 10 machines of the same model may be positioned in a clinic for use by different patients each requiring a different set of dialysis fluids and components. To avoid cross-contamination, the machines can be limited to provide therapy for only specified patients or access to particular caregivers or clinicians. These machines of the device ecosystem 100 can provide a plurality of modes, including one or more access-controlled modes, whose access is controlled, for example, by the use of a hardware token 124.

Hardware token 124 could be any suitable device, such as a USB thumb drive, some other USB device known to one of skill, a radio frequency identification (RFID) device, a device that uses some other communication protocol, such as Worldwide Interoperability for Microwave Access (WiMAX), wireless fidelity (Wi-Fi), infrared (IR), Bluetooth, RS-232, RS-485, parallel, serial, or any other protocol known to one of skill. Hardware token 124 can include both a hardware key specific to the token, which can be, for example, immutable and hardcoded into hardware token 124, and can also have stored in a memory thereof a software key, which can include a data structure that provides various fields, including a cryptographic certificate, and an expiry.

User 120 can be an authorized user who has access to restricted modes of operation for secured apparatus 130. User 120 can possess hardware token 124, but until hardware token 124 is provisioned with an appropriate software key, the hardware token 124 may not be valid for operating restricted modes of secured apparatus 130. Thus, the user 120 inserts hardware token 124 into user endpoint device 128, and then queries key server 140 to gain access or operate a user endpoint device 128 (which can be, for example, a laptop computer or desktop computer).

Key server 140 can be a cloud-based service, for example, and can include a certificate authority that issues software keys, validates hardware keys, provisions shared keys, and performs other services. User 120 can access key server 140 via, for example, a web interface, representational state transfer (REST) application programming interfaces (APIs) that communicate with a GUI on user endpoint device 128, or other similar technology. User 120 can provision a software key for hardware token 124, and endpoint device 128 then stores the software key on hardware token 124. Optionally, a user interface such as a GUI can enable user 120 to set an expiry for the software key stored on hardware token 124. Alternatively, key server 140 could provide a default expiry.

In certain embodiments, the key server 140 could provide a shared key or unique certificate to secured apparatus 130. Because key server 140 knows which certificate was provisioned to secured apparatus 130, key server 140 can provision to hardware token 124 a certificate that can only be unlocked by a device having this shared key or certificate. Thus, if all secured apparatus 130 within the ecosystem (such as a clinic or hospital) are provisioned with the same shared key, then a single hardware token 124 can be used to unlock restricted modes on each secured apparatus in the ecosystem.

In certain embodiments, hardware token 124 includes a hard-coded hardware key wherein the hardware key can optionally expire. For example, the hardware token 124 could have an expiry of a time period longer than would traditionally be used, or that would normally be used for a software key. The expiry for hardware token 124 could be on the order of six months, one year, or multiple years. In other embodiments, the hardware token 124 can expire at any desired time period for example, by one or more hour, by one or more day, by one or more week, or by monthly expiry.

When user 120 inserts hardware token 124 into secured apparatus 130, or otherwise places hardware token 124 into communication with secured apparatus 130, secured apparatus 130 validates the hardware keys of hardware token 124. The secured apparatus 130 can then read the software key from the storage of hardware token 124. Once secured apparatus 130 has validated both the hardware key and the software key, then user 120 is authorized via hardware token 124, and secured apparatus 130 can enter a restricted or access-controlled mode.

The systems and methods also describe a hardware token that can be designated with an expiry, after which the hardware token will be invalid. Once the hardware token expires, the token is no longer valid for unlocking a restricted mode on the target device. In an embodiment, a hardware token includes both a hardware key, which can be immutable, as well as a software key (e.g., a digital certificate) stored on a memory of the hardware token. In traditional multifactor authentication, a hardware token is a "something you have" factor, which can be added, for example, to a "something you know" (e.g., a password) factor to provide enhanced authentication. In this case, although the hardware token involves two different keys or certificates, the token does not necessarily provide two-factor authentication. The hardware token and the software key are both "something you have" factors.

During provisioning of the hardware token, the validity of the software token or digital certificate can be configured and set. For example, the software token can have a validity measured on the order of days. In some examples, this can be a time period such as one day, two days, one week, two weeks, one month, 28 days, or some other designated time span. This time span can be measured as a time delta from the time when the software token was created. In other words, the software token can include a data structure that includes both the digital certificate, and an expiry. This expiry can be defined in terms of the date that the hardware token was provisioned, plus a designated time span. Alternatively, a date certain could be added to the hardware token, on which the software token can expire. When the hardware token is used, the validity of the hardware token depends on the software key also being valid and unexpired.

Thus, when a hardware token is presented to the device, the device can perform a two-step verification. First, the device can verify the validity of the hardware token itself, such as by checking a hardware key permanently or immutably stored on the hardware device. This could be stored, for example, via on the hardware token or by some other mechanism. In some cases, the hardware key is not read directly by a device, but rather the hardware token can provision a unique key that is deterministically derived from the hardware key, and that is unique to the reading device. This unique key could be based on a token or key provided by the reading device. Thus, in this embodiment, the hardware key is not directly exposed to outside devices.

In the second step, the validity of the software token contained or stored on the hardware token can also be also verified. For example, the hardware key could be used to decrypt, or check the signature of, the software token. Alternatively, an encryption key, such as a shared key stored on the reading device, could be used to validate the software token. If both validation steps are successful, the hardware token is deemed valid, and the device can allow access to controlled modes.

If the hardware token is lost or stolen, the hard token can be used only for a short time after the loss. The software token carries a self-propagating revocation mechanism. If an adversary or other bad actor attempts to use the hardware token after the expiry of the software token or digital certificate, the attempt will fail. The set expiry can reduce the security risk associated with a lost or stolen hardware token, while also reducing the need for always-on network connections for devices, or for other complicated revocation mechanisms.

The systems and methods generally relate to cybersecurity, and have particular applicability to any type of device. The teachings can be broadly applied to many possible cybersecurity use cases, and in particular, can be applicable to general cybersecurity of any type. In certain non-limiting embodiments, the systems and methods can be used in medical devices where hardware tokens are used to control access to certain modes of the medical devices.

In one illustrative use case, a security token can be used for a non-networked hemodialysis or peritoneal dialysis device. This device could be, by way of illustrative example, a sorbent technology-based hemodialysis system or a peritoneal dialysis system. The technology could also be applicable to other dialysis systems, other biomedical devices, and other general devices. In the use case of the hemodialysis or peritoneal dialysis system, the system has a service mode, and access of the mode is controlled through the use of a USB-based hardware token. Activities like calibration, diagnosis, and software upgrades can be performed by a service user in the service mode of the device. Access can be limited to the service mode to only authorized users, as incorrectly using the service mode could harm the device and/or the patient.

The systems and methods provide a timeframe in which a hardware token is valid. Outside of the timeframe encoded into the software key or software data structure, the hardware token is not valid, and cannot be used on a device for authentication. The software token or digital certificate can have a relatively short duration of validity wherein the software token can be stored in a hardware token by a user during provisioning. This user can be, for example, a service user or other authorized user. This is done before the use of the hardware token on a medical device or other device with cybersecurity features and controlled modes.

In any embodiment, the hardware token is valid as long as the software token and digital certificate remain valid. In any embodiment, the software token and digital certificate can be requested from a software token or digital certificate generation server by the user, such as a service user. The user can set a validity period of the software token or digital certificate. For example, the user could set a period of one day. In any embodiment, a user interface such as a graphical user interface (GUI) can be provided, in which the user can select a validity time for the software token, or alternatively, a default value can be used.

In any embodiment, a plurality of comparable devices (e.g., devices of a similar model or a bank of similar devices) can verify the validity of the software token or digital certificate that is stored in the hardware token. The devices can verify the authenticity and integrity of the software token and digital certificate. Once verified, the devices can determine the period of validity from the payload or data structure stored on the software token. Based on the information retrieved, the devices can determine whether the software token or digital certificate is valid, and thus determine whether the hardware token is still valid.

In any embodiment, devices can allow access to access-controlled modes only if the hardware token presented is valid, including having a valid and unexpired software token. One result can be that a security risk related to abuse of a lost or stolen hardware token can be potentially diminished, because the hardware token is unusable after the validity period has expired. After the expiry, the hardware token becomes valid again only after a new software token or digital certificate is stored in the hardware token by an authorized user.

In any embodiment, the memory of the hardware token can be a read/write memory, in which case, the old software token or other data structures can be overwritten as necessary. Thus, when the validity of the software key expires, there is no need to discard the hardware token. Rather, a new software key can be provisioned for the hardware token, and then the hardware token continued to be used.

The method can reduce patient security risk due to the risk associated with the abuse of a medical device by an adversary who can gain access to a lost or stolen hardware token. Revocation of a lost or stolen hardware token can provide a valuable security feature from a regulatory standpoint, as revocation can reduce the risk to patient safety from a device being abused by an adversary. In any embodiment, the hardware tokens can be revoked for a non-networked device in a non-networked environment. In any embodiment, the hardware token can be revoked in a clinical setting where, for in one non-limiting example, a number of devices (such as 10 devices) do not have to be updated manually. This can be used in a setting for internet connections can be challenging as in some non-first world settings where devices may not practically be networked to every device or together. The teachings of the present specification can remove the burden of updating all the medical devices in the case of revocation of a token. Furthermore, although the teachings are provided in the context of a dialysis machine, the teachings can also be used in multiple types of devices.

Hardware Token

Figure 2:
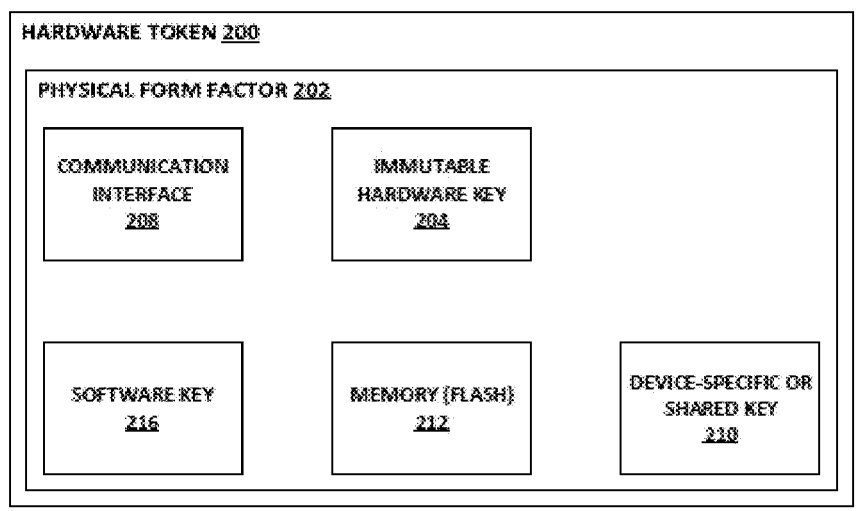
FIG. 2 is a block diagram of a hardware token.

FIG. 2 is a block diagram of a hardware token 200 having a physical form factor 202. Hardware token 200 can be any of the devices described in connection with FIG. 1, or throughout this specification. Hardware token 200 can include a hardware key 204. Hardware key 204 can be immutably stored on hardware token 200. Hardware token 200 can also include a communication interface 208. Communication interface 208 provides the appropriate hardware to communicate with a secured apparatus (such as secured apparatus 130 of FIG. 1), or some other apparatus. Communication interface 208 can include both the hardware, and a software stack for providing the communication. Optionally, hardware token 200 could include a device specific key 210. Device specific key 210 could be used to authenticate hardware token 200 to a specific secured apparatus.

The device specific key 210 can be used in a case where hardware token 200 is intended to be used with only a single apparatus. The device specific key 210 could then be used to sign, encrypt, or otherwise validate a certificate or other part of the software key 216. For example, the device specific key 210 could be a public key that corresponds to a private key of the secured apparatus. The public key-private key combination can then be used to verify the signature on a data structure.

Hardware token 200 can also include a memory 212. Memory 212 can include a volatile memory, and can also include a nonvolatile memory. For example, flash can be used as a nonvolatile memory technology. A software key 216 can be stored in the nonvolatile memory, such as flash memory. Software key 216 can include a data structure, including, for example, a signed certificate, as well as an expiry for software key 216.

Medical Device

Figure 3:
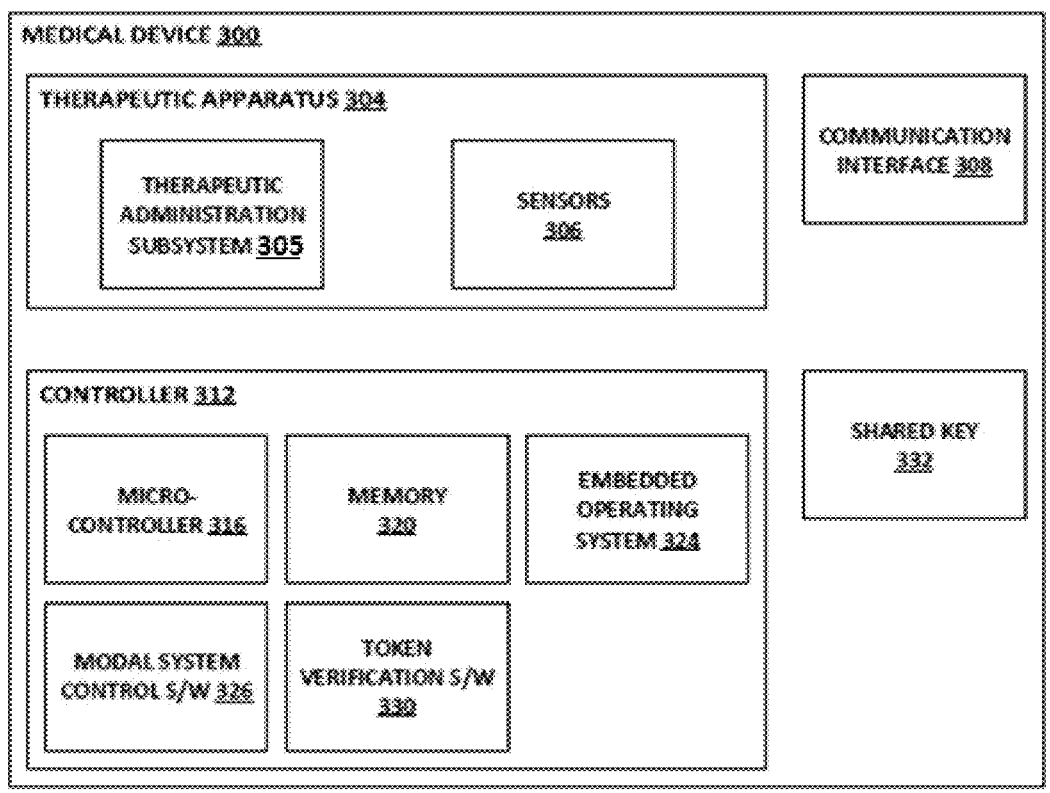
FIG. 3 is a block diagram of a medical device.

FIG. 3 is a block diagram of a medical device 300. The medical device 300 is an example of a secured apparatus, such as secured apparatus 130 of FIG. 1. Medical device 300 is provided here as a concrete example of a secured apparatus, and other examples could be used. In this example, medical device 300 is configured to provide a plurality of modes, including a restricted or accessed-secured mode.

Medical device 300 includes a therapeutic apparatus 304, which includes a therapeutic administration subsystem 305, and sensors 306. Therapeutic administration subsystem 305 can administer treatments or substances to a patient. For example, the therapeutic administration subsystem 305 could deliver medications intravenously or otherwise, could provide dialysis, including filtering of blood, or could provide any other type of medical therapy. Sensors 306 can be provided incident to therapeutic administration subsystem 305, or alternatively, sensors 306 could be the primary purpose of the medical device 300. For example, in a pulse oximeter or blood pressure cuff, sensors 306 would provide a primary function. In the case of a dialysis machine, such sensors could be used as secondary inputs to aid in dialysis.

The medical device 300 can include a communication interface 308. Communication interface 308 could include an always-on internet connection, but can include a non-networked connection, or a network connection that is used to configure medical device 300, but that is not generally connected during use. For example, during configuration, communication interface 308 could be used to provide a private key for medical device 300, a shared key (e.g., one shared between multiple similar devices of a class), or a key pair. Communication interface 308 can also provide a hardware and a software stack to interface with a hardware token, such as hardware token 200 of FIG. 2.

Medical device 300 can include a controller 312. Controller 312 can include hardware and software to provide control functions, including for providing a plurality of modes. In any embodiment, controller 312 can be based on a microcontroller 316, and also include a memory 320. An embedded operating system 324 provides low-level drivers and functions for operational software, which can include modal system control software 326. The modal system control software 326 enforces modal controls for the various modes provided by medical device 300. Token verification software 330 can include, for example, a cryptographic subsystem that can be used to decrypt devices according to a key, or that can perform attestation or some other cryptographic operation that is used to verify the signature of a device. In any embodiment, a shared key 332 is provided, and can be shared between various devices of a class, as described herein.

Form Factor Perspective View of Hardware Token

Figure 4:
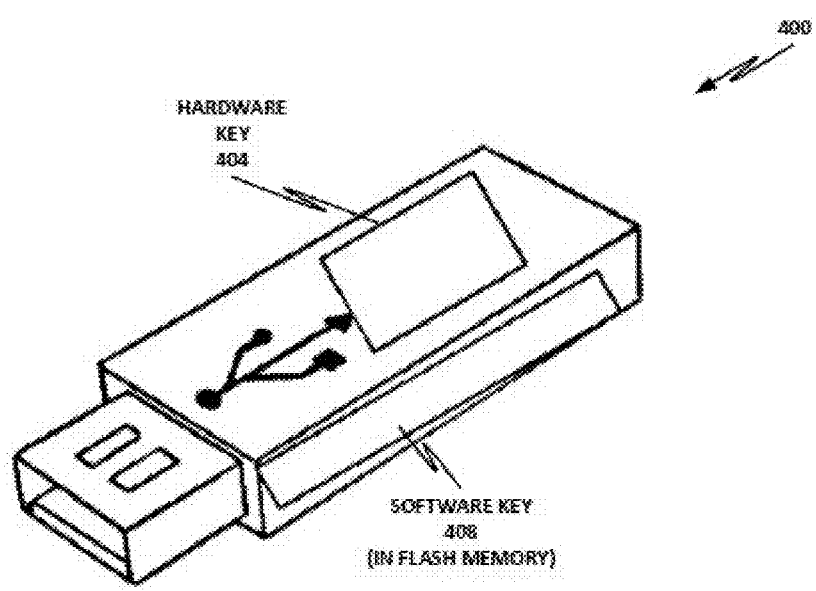
FIG. 4 is a perspective view illustrating a form factor of a hardware token.

FIG. 4 is a perspective view illustrating a form factor of a hardware token 400. In this case, hardware token 400 has the physical form factor of a USB thumb drive. Hardware token 400 includes a hardware key 404 and a software key 408 stored in a flash memory of the USB thumb drive. The hardware token 400 can be in any suitable shape, form, or size known to one of skill in the art can be used.

Illustrative Data Structure

Figure 5:
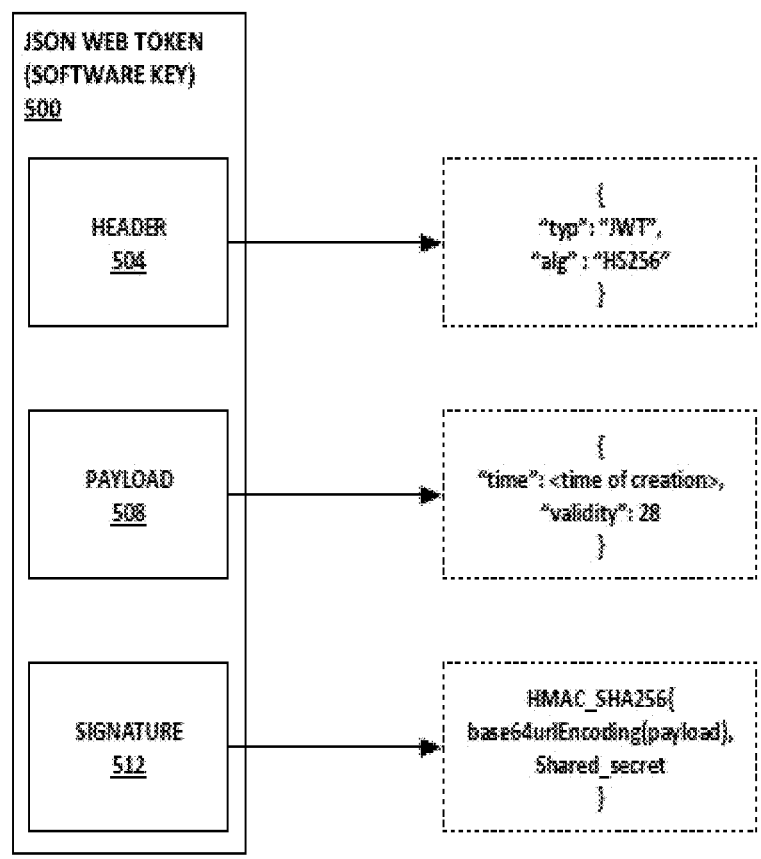
FIG. 5 is a block diagram of an illustrative data structure.

FIG. 5 is a block diagram of an illustrative data structure that can be used to provide a software key. In this example, software key 500 can be a JavaScript Object Notation (JSON) web token that is being used as a software token. JSON software key 500 includes a header 504, a payload 508, and a signature 512. Also illustrated herein are example data structures that could be used for header 504, payload 508, and signature 512, respectively. One of skill will understand that any other suitable data structure can be used.

Method to Initially Provision a Software Key

Figure 6:
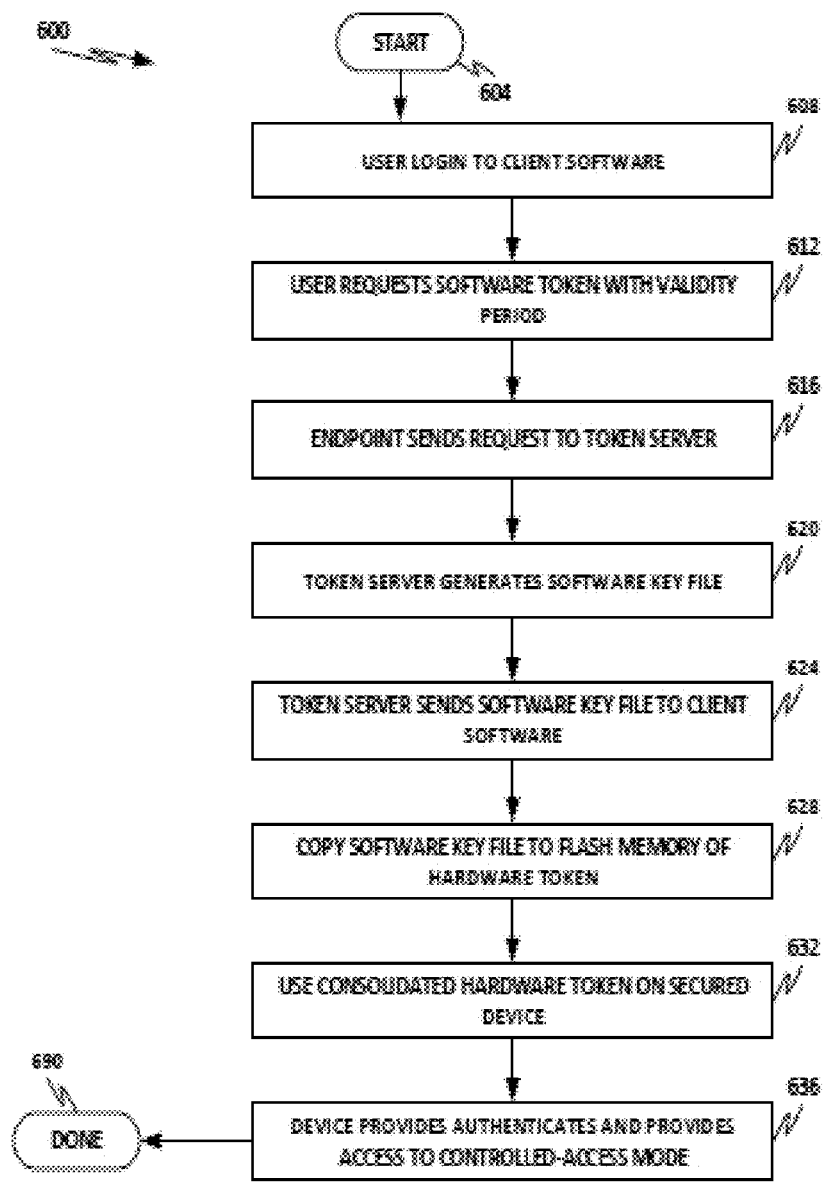
FIG. 6 is a flowchart of a method.

FIG. 6 is a flowchart of a method 600. Method 600 can be used to initially provision a software key onto a hardware token.

Starting in block 604, the user procures the hardware token.

In block 608, the user logs in to client software, such as on a user endpoint device.

In block 612, the user requests a software token. For example, this could be requested via a web interface, or via a GUI that uses REST APIs, or other similar protocols. Using this interface, the user requests a software token, and provides a validity period for the software token as an input. Alternatively, a default validity could be used.

In block 616, the user request is sent to a software token server.

In block 620, the software token server generates a software token file, per the user request.

In block 624, the software token server sends the software token file to the client software as a payload via the network.

In block 628, the user or the endpoint device copies the software token to the hardware token, such as by copying the software token to the flash memory of the hardware token. This could be done by the user downloading the token and manually copying over, or by the user interface program automatically detecting the hardware token and copying the software token over.

In block 632, the user can use this consolidated security token (including the hardware token with the provisioned software key) on a secured device.

In block 636, the device provides access to the access-controlled modes and functionalities when a valid security token is inserted, or otherwise presented.

In block 690, the method is done.

Validation of a Hardware Token

Figure 7:
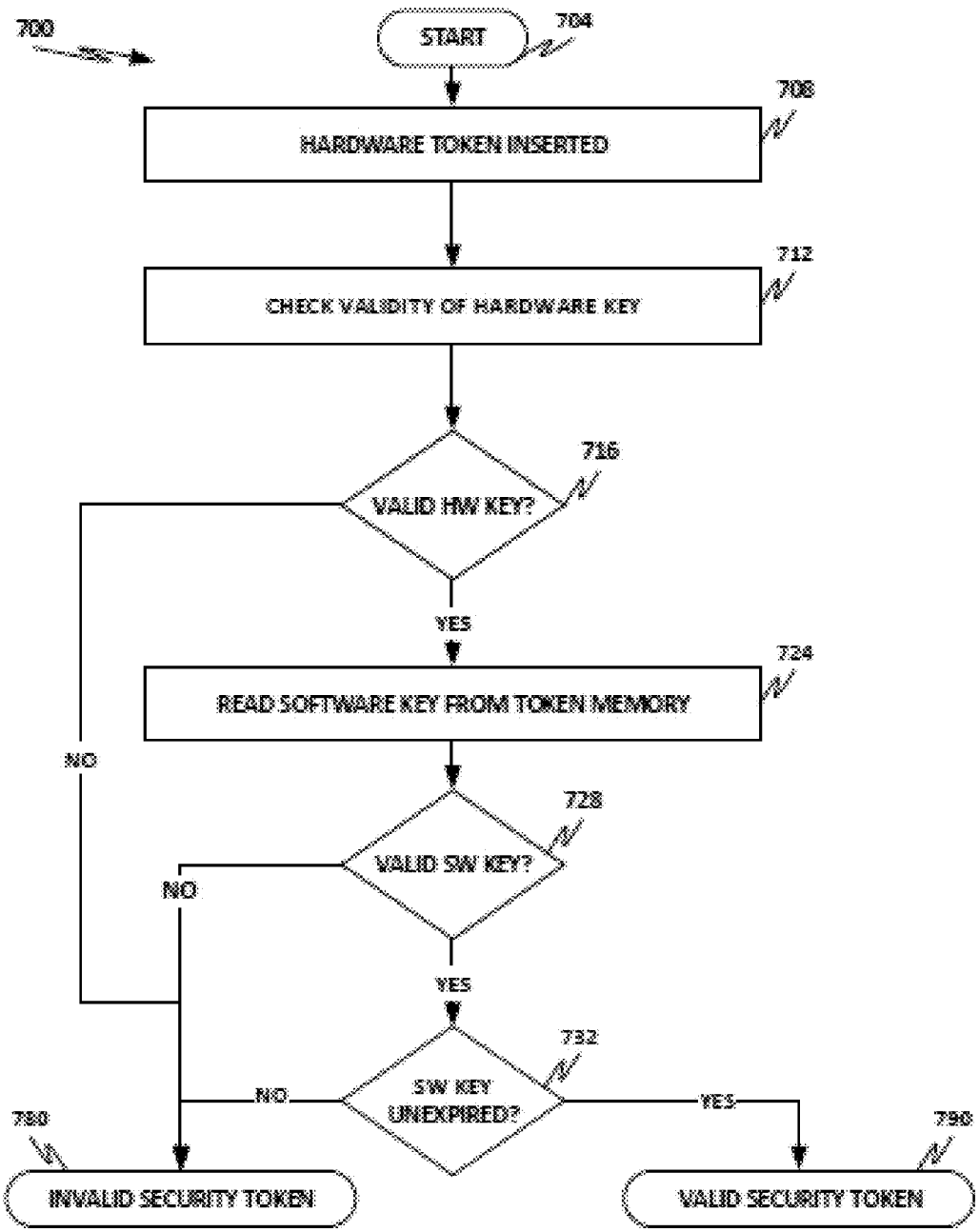
FIG. 7 is a flowchart of an additional method.

FIG. 7 is a flowchart of a method 700. Method 700 can include validation of a hardware token presented to a device, such as a secured device.

Starting in block 704, at block 708, the hardware token is inserted into the device, proximity is detected, or otherwise placed in communication with the secured device.

In block 712, the device verifies the validity of the hardware token itself. This can be done, for example, by extracting a hardware key from the hardware token, or by receiving an automatically generated hardware key that is based on a key held by the secured device, and that is further based on an immutable hardware key stored on the hardware token that is not directly readable.

In decision block 716, the secured device determines whether the hardware token is valid.

If the token is not valid, then in block 780, the security token is rejected, and the access-controlled mode is not unlocked by the token.

Returning to decision block 716, if the hardware token is valid, then in block 724, the device reads the software token stored in the hardware token. This can include retrieving the software key from the memory, such as a flash memory.

In decision block 728, the device determines whether the software token is valid. This could include decrypting or verifying a certificate in the software token via the hardware key provided by the hardware token, or by including the use of a shared key stored on the device to cryptographically validate or decrypt the software key data structure.

If the software key is not authentic, and the integrity has not been maintained, then in block 780, the hardware token can be rejected, and access-controlled mode is not unlocked.

Returning to decision block 728, if the software token is authentic and has maintained integrity, then in block 732, the device checks to see whether the software token has expired. For example, the device can extract an expiry from the software key, such as one stored in the software key data structure. This expiry could be signed to make it harder for a bad actor to tamper with the expiry after gaining access to the hardware token. Alternatively, the software token could be encrypted, and can be decrypted, for example, via a shared key stored on the secured device, so that again, it is difficult for a bad actor to tamper with the software key.

If the software token has expired, then in block 780, the hardware token is rejected, and the secured access mode is not unlocked.

Returning to decision block 732, if the software token is valid and unexpired, then in block 790, the hardware token is deemed valid, and a secured access mode can be unlocked.

Validation of a Software Token

Figure 8:
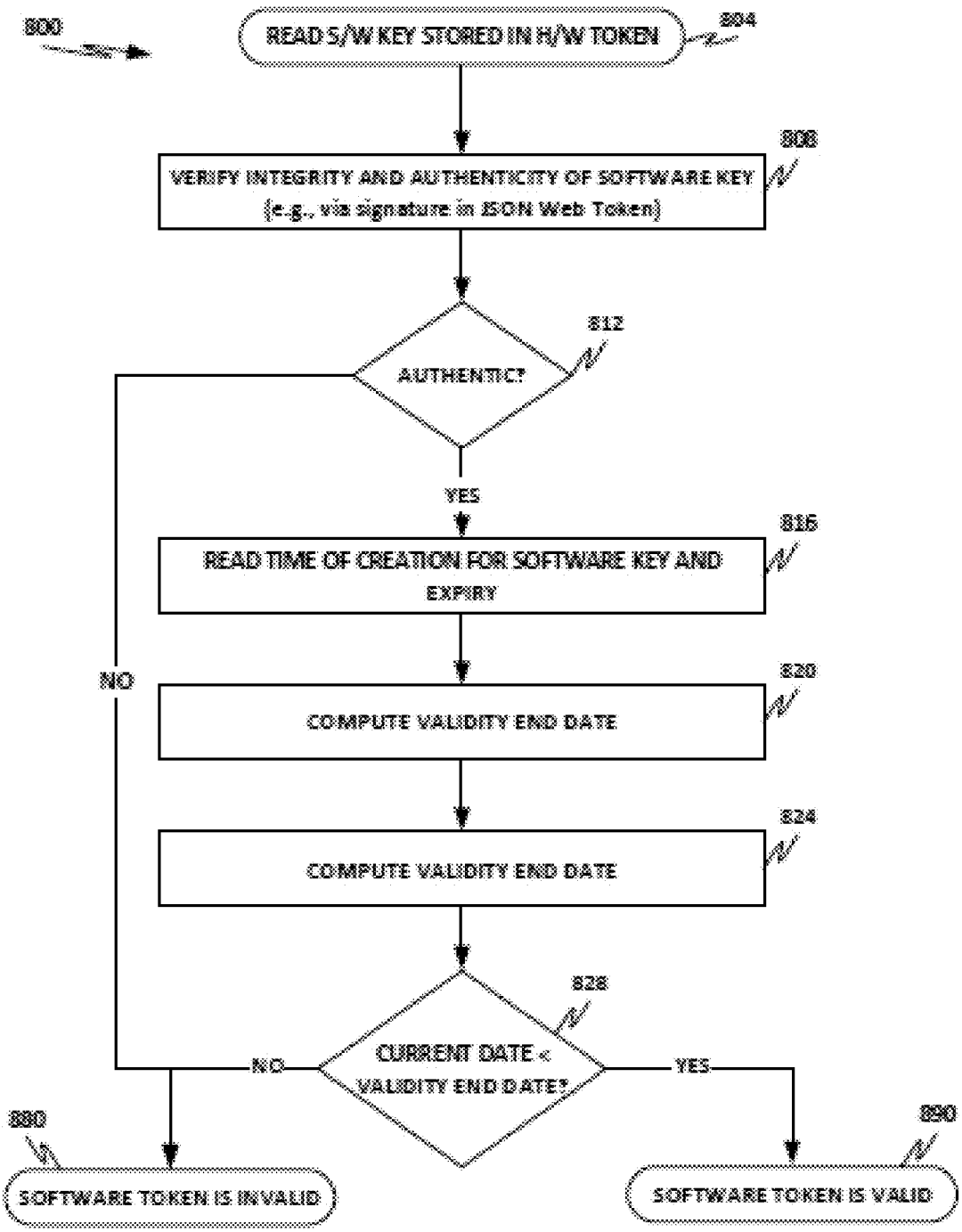
FIG. 8 is a flowchart of a further additional method.

FIG. 8 is a flowchart of a method 800. Method 800 can include an example method of validating a software token that has been stored on a hardware key. Method 800 could be used in place of any of the operations illustrated throughout this specification where a software key is to be validated.

In block 804, the secured device reads the software token stored in the hardware token, such as on a flash memory.

In block 808, the device verifies the integrity and authenticity of the software token. For example, one method of verifying is based on the signature stored in a JSON web token software key. Alternatively, the software token could be decrypted, or otherwise cryptographically verified.

In decision block 812, the device determines whether the software token is authentic and the integrity has been maintained.

If integrity has not been maintained, then in block 880, the software token is deemed invalid.

Returning to decision block 812, if the software token is authentic and has maintained integrity, then in block 816, the device reads the time of creation of the software key, and the validity period of the software key. For example, this can include reading the time of creation and the validity period from a payload field of a JSON web token.

In block 820, the device computes the validity end date and time of the software token by adding the validity period to the time of creation.

In block 824, the device compares the validity end date and time with the current date and time.

In decision block 828, the device determines whether the current date and time is less than the validity end date and time calculated in the previous operations. If the current date and time is not less than the validity end date and time calculated in the previous operations, then in block 880, the software token is deemed invalid.

Returning to decision block 828, if the current date and time is less than the valid end date and time, then in block 890, the software token is deemed valid.

One skilled in the art will understand that various combinations and/or modifications and variations can be made in the described systems and methods depending upon the specific needs for operation. Various aspects disclosed herein can be combined in different combinations than the combinations specifically presented in the description and accompanying drawings. Moreover, features illustrated or described as being part of an aspect of the disclosure can be used in the aspect of the disclosure, either alone or in combination, or follow a preferred arrangement of one or more of the described elements. Depending on the example, certain acts or events of any of the processes or methods described herein can be performed in a different sequence, can be added, merged, or left out altogether (e.g., certain described acts or events cannot be necessary to carry out the techniques). In addition, while certain aspects of this disclosure are described as performed by a single module or unit for purposes of clarity, the techniques of this disclosure can be performed by a combination of units or modules associated with, for example, a device.

What is claimed is:

1. A system comprising an apparatus programmed to provide a plurality of modes, and a security token, wherein the security token comprises:
   a communication interface, including a communication transceiver;
   a circuit having encoded thereon an immutable hardware key; and
   a tangible, nonvolatile memory, the nonvolatile memory having stored thereon a mutable software key, the mutable software key including a cryptographic key and an expiry for the cryptographic key;
   and wherein the apparatus comprises:
   a processor and a memory;
   a communication interface; and
   instructions encoded within the processor to:
   provide the plurality of modes, including a restricted mode;
   detect the security token via the communication interface;
   cryptographically verify the immutable hardware key of the security token; and
   activate the restricted mode after verifying that the mutable software key is valid and unexpired;
   and wherein the system further comprises a therapeutic subsystem to administer a therapeutic treatment to a patient, wherein the restricted mode comprises a therapy administration mode.

2. The system of claim 1, wherein the system is a dialysis machine.

3. The system of claim 1, wherein cryptographically verifying the immutable hardware key comprises verifying that the immutable hardware key has not expired.

4. The system of claim 1, wherein verifying that the mutable software key is valid and unexpired comprises extracting the expiry from the mutable software key.

5. The system of claim 1, wherein verifying that the mutable software key is valid and unexpired comprises cryptographically validating the mutable software key.

6. The system of claim 5, wherein cryptographically validating the mutable software key comprises validating the mutable software key via the immutable hardware key.

* * * * *